(12) United States Patent
Makimura et al.

(10) Patent No.: US 7,781,618 B2
(45) Date of Patent: Aug. 24, 2010

(54) UNSATURATED ALIPHATIC PRIMARY AMINE AND PRODUCTION METHOD THEREOF

(75) Inventors: Michito Makimura, Tokyo (JP); Hiroyuki Izumoto, Tokyo (JP)

(73) Assignee: Lion Akzo Co., Ltd., Yokkaichi-shi (JP)

( * ) Notice: Subject to any disclaimer, the term of this patent is extended or adjusted under 35 U.S.C. 154(b) by 247 days.

(21) Appl. No.: 12/073,422

(22) Filed: Mar. 5, 2008

(65) Prior Publication Data

US 2008/0167497 A1   Jul. 10, 2008

Related U.S. Application Data

(63) Continuation of application No. PCT/JP2006/317010, filed on Aug. 29, 2006.

(30) Foreign Application Priority Data

Sep. 6, 2005   (JP) .............................. 2005-258497

(51) Int. Cl.
*C07C 209/48* (2006.01)
(52) U.S. Cl. ...................... 564/493; 564/491
(58) Field of Classification Search .................. 564/493
See application file for complete search history.

(56) References Cited

U.S. PATENT DOCUMENTS

| | | | | |
|---|---|---|---|---|
| 2,784,232 A | * | 3/1957 | Terry et al. | ................. 564/490 |
| 5,097,073 A | * | 3/1992 | Abe et al. | ................... 564/493 |

FOREIGN PATENT DOCUMENTS

| | | |
|---|---|---|
| JP | 62-175445 | 8/1987 |
| JP | 04-266859 | 9/1992 |
| JP | 05-017415 | 1/1993 |
| JP | 2001-226327 | 8/2001 |

OTHER PUBLICATIONS

Database CAPLUS on STN, Acc. No. 2001:603527, JP 2001226327 (Aug. 21, 2001) (abstract).*

* cited by examiner

*Primary Examiner*—Brian J Davis
(74) *Attorney, Agent, or Firm*—Edwards Angell Palmer & Dodge LLP

(57) ABSTRACT

The present invention relates to a method for producing an unsaturated aliphatic primary amine including subjecting an unsaturated aliphatic nitrile having 16 to 22 carbon atoms to hydrogen reduction in the presence of ammonia using a hydrogenation catalyst to produce an unsaturated aliphatic primary amine, wherein 0.01 parts by weight to 1.0 part by weight of aromatic carboxylic acid amide is added based on 100 parts by weight of the unsaturated aliphatic nitrile, and a partial pressure ratio of ammonia to hydrogen is adjusted to 8/2 to 6/4. The present invention also relates to an unsaturated aliphatic primary amine, which is produced by the production method.

2 Claims, No Drawings

UNSATURATED ALIPHATIC PRIMARY AMINE AND PRODUCTION METHOD THEREOF

CROSS-REFERENCE TO RELATED APPLICATION

This is a continuation of application Ser. No. PCT/JP2006/317010, filed on Aug. 29, 2006.

BACKGROUND OF THE INVENTION

1. Field of the Invention

The present invention relates to a method for producing an unsaturated aliphatic primary amine that involves subjecting an unsaturated aliphatic nitrile to hydrogen reduction to produce an unsaturated aliphatic primary amine with a high amine conversion rate and iodine value retention rate; and to an unsaturated aliphatic primary amine produced by the method for producing an unsaturated aliphatic primary amine.

2. Description of the Related Art

Unsaturated long-chain aliphatic primary amines are useful substances that find various applications as intermediates of surfactants, dispersants, agricultural chemicals, disinfectants, antistatic agents, textile treating agents, etc.

In general, it is known that amines having long-chain alkyl chains are produced by subjecting long-chain aliphatic nitrites, derived from natural fats and oils, to hydrogen reduction, by which a mixture of primary, secondary, and tertiary amines are obtained.

In the reaction where unsaturated long-chain aliphatic nitrile is subjected to hydrogen reduction using a hydrogenation catalyst to convert to an unsaturated long-chain aliphatic primary amine, promotion of reduction reaction of a nitrile group to an amino group results in the increase of hydrogenation rate of unsaturated bonds in hydrocarbon chains. As a result, in addition to the unsaturated long-chain aliphatic primary amine, a saturated long-chain aliphatic primary amine is obtained as a by-product. Therefore, unsaturated long-chain aliphatic primary amines cannot be obtained in high selectivity. On the other hand, if hydrogenation rate of unsaturated bonds in hydrocarbon chains is reduced, it is difficult to obtain an unsaturated long-chain aliphatic primary amine in high selectivity.

As a method for producing an aliphatic primary amine by is hydrogenating nitrile compounds, methods disclosed in Japanese Patent Application Publication (JP-B) No. 38-21353 and Japanese Patent Application Laid-Open (JP-A) 04-266859. In the method disclosed in JP-B No. 38-21353, the aliphatic primary amine is produced using a hydroxide of alkali metal or alkaline earth metal, or an alcoholate or amide of those metals. Specific products disclosed are amines having 5 to 9 carbon atoms. The method disclosed in JP-A No. 04-266859 is related to the production method of saturated aliphatic primary amine. Since the primary amines prepared by these methods have a high solidification point (pour point), there are problems. Particularly when derivatized primary amines are used, they are difficult to handle.

To solve this problem, a method for producing an unsaturated aliphatic primary amine with a low pour point is proposed (See JP-A No. 2001-226327). The method described in JP-A No. 2001-226327, however, may generate a saturated long-chain aliphatic primary amine as a by-product as a result of hydrogenation of unsaturated bonds in hydrocarbon chains. In addition, when an aliphatic amide is added, it is difficult to remove by filtration after the reaction, and turbidity, scum, or the like may be generated in the products.

Thus, in the present situation, a method that suppresses the generation of saturated aliphatic primary amine as a by-product, does not generate turbidity or scum in the product, and can produce an unsaturated aliphatic primary amine with a low solidification point efficiently has not been provided, and there is a desire for further improvement.

BRIEF SUMMARY OF THE INVENTION

An object of the present invention is to solve the conventional problems and to achieve the following objects. Specifically, an object of the present invention is to provide a method for producing an unsaturated aliphatic primary amine that suppresses the generation of saturated aliphatic primary amine as a by-product, generates no turbidity or scum in the product, and can produce an unsaturated aliphatic primary amine with a low solidification point efficiently; and to provide an unsaturated aliphatic primary amine produced by the method for producing an unsaturated aliphatic primary amine.

As a result of dedicated investigations conducted by the present inventors to settle the above-mentioned problems, they have found that when an unsaturated aliphatic primary amine is produced by subjecting an unsaturated aliphatic nitrile to hydrogen reduction in the presence of ammonia, addition of aromatic carboxylic acid amide and a partial pressure ratio of ammonia to hydrogen (hereinafter, referred to as "pressure ratio") of 8/2 to 6/4 suppresses the generation of saturated aliphatic primary amine as a by-product, generates no turbidity or scum, and can produce an unsaturated aliphatic primary amine with a low solidification point efficiently, and have accomplished the present invention.

The present invention is based on the above-mentioned findings by the present inventors, and means for solving the above-mentioned problems are as follows. Specifically, <1> A method for producing an unsaturated aliphatic primary amine including subjecting an unsaturated aliphatic nitrile having 16 to 22 carbon atoms to hydrogen reduction in the presence of ammonia using a hydrogenation catalyst to produce an unsaturated aliphatic primary amine, wherein 0.01 parts by weight to 1.0 part by weight of aromatic carboxylic acid amide is added based on 100 parts by weight of the unsaturated aliphatic nitrile, and a pressure ratio of ammonia to hydrogen is adjusted to 8/2 to 6/4.

<2> The method for producing an unsaturated aliphatic primary amine according to the <1>, wherein the aromatic carboxylic acid amide is one of para-toluamide and benzamide.

<3> The method for producing an unsaturated aliphatic primary amine according to one of the <1> and <2>, wherein the amount of aromatic carboxylic acid amide to be added is 0.05 parts by weight to 0.50 parts by weight based on 100 parts by weight of the unsaturated aliphatic nitrile.

<4> An unsaturated aliphatic primary amine, which is produced by the method for producing an unsaturated aliphatic primary amine of any one of <1> to <3>, wherein the unsaturated aliphatic primary amine has an amine conversion rate, expressed by the following formula (1), of 95% or more, and has an iodine value retention rate, expressed by the following formula (2), of 95% or more:

$$\text{Amine conversion rate(\%)} = \frac{\begin{pmatrix} \text{Found amine value of} \\ \text{unsaturated aliphatic} \\ \text{primary amine} \end{pmatrix}}{\begin{pmatrix} \text{Theoretical amine value} \\ \text{of unsaturated aliphatic} \\ \text{primary amine} \end{pmatrix}} \times 100 \quad \text{formula (1)}$$

$$\text{Iodine value retention rate(\%)} = \frac{\begin{pmatrix} \text{Iodine value} \\ \text{of} \\ \text{unsaturated} \\ \text{aliphatic} \\ \text{primary amine} \end{pmatrix} \times \begin{pmatrix} \text{Molecular} \\ \text{weight of} \\ \text{amine} \end{pmatrix}}{\begin{pmatrix} \text{Iodine value} \\ \text{of} \\ \text{unsaturated} \\ \text{aliphatic nitrile} \end{pmatrix} \times \begin{pmatrix} \text{Molecular} \\ \text{weight of} \\ \text{nitrile} \end{pmatrix}} \times 100 \quad \text{formula (2)}$$

The present invention can provide a method for producing an unsaturated aliphatic primary amine that suppresses the generation of saturated aliphatic primary amine as a by-product, does not generate turbidity or scum in the product, and can produce an unsaturated aliphatic primary amine with a low solidification point efficiently; and provide an unsaturated aliphatic primary amine produced by the method for producing an unsaturated aliphatic primary amine.

DETAILED DESCRIPTION OF THE INVENTION (Method for Producing an Unsaturated Aliphatic Primary Amine)

The method for producing an unsaturated aliphatic primary amine of the present invention comprises subjecting an unsaturated aliphatic nitrile having 16 to 22 carbon atoms to hydrogen reduction in the presence of ammonia using a hydrogenation catalyst to produce an unsaturated aliphatic primary amine, wherein 0.01 parts by weight to 1.0 part by weight of aromatic carboxylic acid amide is added based on 100 parts by weight of the unsaturated aliphatic nitrile, and a pressure ratio of ammonia to hydrogen is adjusted to 8/2 to 6/4.

-Unsaturated Aliphatic Nitrile-

In the method for producing an unsaturated aliphatic primary amine of the present invention, the unsaturated aliphatic nitrile to be used as a raw material (hereinafter, may be referred to as "nitrile of starting material") is not particularly limited as long as it has 16 to 22 carbon atoms, can be appropriately selected according to the purpose, and is preferably an unsaturated long-chain aliphatic nitrile having 18 to 22 carbon atoms.

The unsaturated aliphatic nitrile may be a mixture of nitrites having different carbon atoms.

Examples of the unsaturated aliphatic nitrile include those produced from corresponding fatty acids by the known methods; specific examples of the unsaturated aliphatic nitrile include those produced from oleic acid, linoleic acid, linolenic acid, erucic acid; and fatty acids induced from animal and vegetable oils and fats such as tallow fatty acid, soya fatty acid, palm oil fatty acid, tall oil fatty acid, and rape fatty acid.

Among these, unsaturated aliphatic nitrites derived from oleic acid and erucic acid are preferable; specific examples thereof include oleonitrile and erucanitrile.

-Hydrogenation Catalyst-

The hydrogenation catalyst is not particularly limited and can be appropriately selected from known hydrogenation reaction catalysts. Examples thereof include nickel catalysts, copper catalysts, precious metal catalysts, and the like.

Among these, nickel catalysts are preferable. Particularly, nickel catalysts supported on the carrier are more preferable in terms of e.g. handleability and cost; examples thereof include nickel-kieselguhr catalyst, nickel-alumina catalyst, nickel silica-alumina catalyst, and the like.

The amount of the hydrogenation catalyst used is preferably 0.01 parts by weight to 2.0 parts by weight, and more preferably 0.1 parts by weight to 0.5 parts by weight based on 100 parts by weight of the nitrites of starting material. If the amount of the hydrogenation catalyst used is less than 0.01 parts by weight, the conversion rate from the nitrile of starting material to amine may become worse. If it is more than 2.0 parts by weight, the resulting unsaturated aliphatic primary amine may have a remarkably reduced iodine value retention rate.

-Aromatic Carboxylic Acid Amide-

For the aromatic carboxylic acid amide, for example, para-toluamide and benzamide are preferable.

By adding the aromatic carboxylic acid amide in an amount of 0.01 parts by weight to 1.00 parts by weight based on 100 parts by weight of the nitrites of starting material, an effect to prevent the hydrogenation of unsaturated bonds in hydrocarbon chains can be obtained and generation of saturated aliphatic primary amine as a by-product can be reduced. In addition, reduction reaction of the nitrile of the starting material is not inhibited and yield of unsaturated aliphatic primary amine is improved.

If the amount of the aromatic carboxylic acid amide added is less than 0.01 parts by weight based on 100 parts by weight of the nitrites of starting material, the iodine value of the unsaturated aliphatic primary amine may be lowered, resulting in the iodine value retention rate being less than 95% sometimes. If the amount added is more than 1.00, the activity of the hydrogenation catalyst is inhibited, resulting in the remarkable decrease in conversion rate from the nitrile of starting material to amine sometimes. The amount of the aromatic carboxylic acid amide added is more preferably 0.01 parts by weight to 0.80 parts by weight, and particularly preferably 0.05 parts by weight to 0.50 parts by weight based on 100 parts by weight of the nitrites of starting material.

-Ammonia-

In the method for producing an unsaturated aliphatic primary amine, in order to obtain an unsaturated aliphatic primary amine as a main product, ammonia is allowed to be present in a reaction system to perform a reaction to convert the nitrites of starting material to amines.

The amount of ammonia used is preferably 5.5 parts by weight to 8.5 parts by weight based on 100 parts by weight of the nitrile of starting material.

By adjusting the partial pressure of the ammonia in a reaction system to a pressure ratio of ammonia to hydrogen of 8/2 to 6/4, unsaturated aliphatic primary amine with a high iodine value retention rate can be produced efficiently.

If the pressure ratio of ammonia to hydrogen is more than 8/2, the progress of conversion reaction to amines is remarkably slow, making it difficult to produce the unsaturated aliphatic primary amine sometimes. On the other hand, if the pressure ratio is less than 6/4, the amount of secondary amine and tertiary amine generated as a by-product increases, and in addition, the iodine value retention rate may be lowered.

<Conversion Reaction to Amines>

The conversion reaction to amines is a reaction in which the nitrites of starting material are converted to amines. Specifically, the nitrile of starting material, the hydrogenation catalyst, and the aromatic carboxylic acid amide are placed in a reaction vessel, and while stirring these in the presence of ammonia, the nitrile of starting material and hydrogen are allowed to react.

The temperature condition of the conversion reaction to amines is preferably 80° C. to 200° C., more preferably 100° C. to 180° C., and most preferably 130° C. to 170° C.

The reaction time of the conversion reaction to amines is preferably 1 hour to 5 hours.

The hydrogen pressure in the conversion reaction to amines is preferably a gauge pressure of 0.5 MPa to 7.0 MPa, and more preferably a gauge pressure of 1.0 MPa to 4.0 MPa. If the hydrogen pressure is less than 0.5 MPa, the progress of reaction is remarkably slow. If the hydrogen pressure is more than 7.0 MPa, the iodine value retention rate of the unsaturated aliphatic primary amine to be obtained is low.

After the conversion reaction to amines, the product obtained is cooled and filtered to separate the hydrogenation catalyst.

The filtration can be performed by any method without limitation and the method can be appropriately selected from known methods. Examples thereof include pressure filtration using e.g. a solid-liquid separation equipment; and the like.

The method for producing an unsaturated aliphatic primary amine of the present invention suppresses the generation of saturated aliphatic primary amine as a by-product, does not generate turbidity or scum in the product, and can produce an unsaturated aliphatic primary amine with a low solidification point efficiently. Thus, the method for producing an unsaturated aliphatic primary amine of the present invention is extremely useful as a method for producing an unsaturated aliphatic primary amine in industrial scale.

(Unsaturated Aliphatic Primary Amine)

The unsaturated aliphatic primary amine prepared by the method for producing an unsaturated aliphatic primary amine of the present invention has an amine conversion rate, expressed by the following formula (1), of 95% or more, and has an iodine value retention rate, expressed by the following formula (2), of 95% or more.

-Amine Conversion Rate- $$\text{Amine conversion rate}(\%) = \frac{\begin{pmatrix} \text{Found amine value of} \\ \text{unsaturated aliphatic} \\ \text{primary amine} \end{pmatrix}}{\begin{pmatrix} \text{Theoretical amine value} \\ \text{of unsaturated aliphatic} \\ \text{primary amine} \end{pmatrix}} \times 100 \quad \text{formula (1)}$$

As shown in formula (1), the amine conversion rate is the rate of found amine value to theoretical amine value of the unsaturated lo aliphatic primary amine prepared by the method for producing an unsaturated aliphatic primary amine of the present invention. The amine conversion rate is more preferably 97% or more and most preferably 98% or more.

The found amine value can be obtained by any measuring method without limitation and the measuring method can be appropriately selected from known methods. For example, 1 g of unsaturated aliphatic primary amine obtained is precisely weighed, dissolved in ethanol and then the amine value is measured using a potentiometric titrator, or the like.

-Iodine Value Retention Rate- $$\text{Iodine value retention rate}(\%) = \frac{\begin{pmatrix} \text{Iodine value} \\ \text{of} \\ \text{unsaturated} \\ \text{aliphatic} \\ \text{primary amine} \end{pmatrix} \times \begin{pmatrix} \text{Molecular} \\ \text{weight of} \\ \text{amine} \end{pmatrix}}{\begin{pmatrix} \text{Iodine value} \\ \text{of} \\ \text{unsaturated} \\ \text{aliphatic nitrile} \end{pmatrix} \times \begin{pmatrix} \text{Molecular} \\ \text{weight of} \\ \text{nitrile} \end{pmatrix}} \times 100 \quad \text{formula (2)}$$

As shown in formula (2), the iodine value retention rate is the rate of iodine value of unsaturated aliphatic primary amine obtained to iodine value of unsaturated aliphatic nitrile, as a raw material. The iodine value retention rate is more preferably 97% or more and most preferably 98% or more.

The iodine value can be measured by any method without limitation and the method can be appropriately selected from known methods; examples thereof include wijs-cyclohexane method, and the like.

When the iodine value retention rate is calculated, it is necessary to convert iodine values to molecular weight.

-Purity (Selectivity to Primary Amine)-

The purity of the unsaturated aliphatic primary amine in the amines prepared by the method for producing an unsaturated aliphatic primary amine (selectivity to primary amine) can be calculated from the found amine value obtained for the amine conversion rate and the found amine values measured after blocking primary amine by reacting with salicylaldehyde (secondary+tertiary amine value).

The purity is preferably 90% or more and more preferably 95% or more.

-Solidification Point-

The solidification point of the unsaturated aliphatic primary amine is preferably less than 10° C.

The unsaturated aliphatic primary amine is of high quality and is excellent in handleability. Thus, the unsaturated aliphatic primary amine can suitably be used in a variety of applications as an intermediate of surfactant, dispersant, agricultural chemical, disinfectant, antistatic agent, textile treating agent, etc.

EXAMPLES

Hereinafter, Examples of the present invention will be described, which however shall not be construed as limiting the present invention thereto.

Examples 1 to 12

Into a 2 liter autoclave equipped with an induction stirrer were charged 600 g of oleonitrile as the nitrile of starting material, 2 g of Ni-kieselguhr catalyst (0.33 parts by weight based on the nitrile of starting material), and para-toluamide or benzamide as the aromatic carboxylic acid amide in an amount shown in Tables 1 and 2, and stirred.

Ammonia and hydrogen were supplied, the reaction temperature was set to 140° C., the reaction pressure was set to a gauge pressure of 3.5 MPa, and ammonia and hydrogen were maintained to the pressure ratio shown in Tables 1 and 2.

While correcting the pressure of hydrogen because decrease in hydrogen pressure due to reduction was observed with heating, reduction reaction had been conducted for about 3.5 hours until decrease in hydrogen pressure was not observed to thereby convert the nitrile of starting material to amine to obtain an unsaturated aliphatic primary amine. For the unsaturated aliphatic primary amine, the amine conversion rate, purity (selectivity to primary amine), iodine value retention rate, and solidification point were evaluated by the following methods, and whether turbidity or scum was generated or not was observed visually. The results are shown in Tables 1 and 2.

<Amine Conversion Rate>

1 g of unsaturated aliphatic primary amine obtained was precisely weighed into a beaker and dissolved in ethanol. The amine value was measured using a potentiometric titrator (model number: COM-980, manufactured by Hiranuma Sangyo Co., Ltd.) to obtain found amine value. From the found value and theoretical value, the amine conversion rate was determined according to the following formula (1).

$$\text{Amine conversion rate}(\%) = \frac{\begin{pmatrix} \text{Found amine value of} \\ \text{unsaturated aliphatic} \\ \text{primary amine} \end{pmatrix}}{\begin{pmatrix} \text{Theoretical amine value} \\ \text{of unsaturated aliphatic} \\ \text{primary amine} \end{pmatrix}} \times 100 \quad \text{formula (1)}$$

<Purity (Selectivity to Primary Amine)>

1 g of unsaturated aliphatic primary amine obtained was precisely weighed into a beaker and allowed to react with salicylaldehyde. The amine value was measured in the same way as described above to determine found secondary+tertiary amine value.

From the found amine value obtained in the measurement of amine conversion rate described above (found total amine value), and found amine values of secondary amine and tertiary amine (found secondary+tertiary amine value), the purity (selectivity to primary amine) was determined according to the following formula (3).

$$\text{Purity}(\%) = \frac{(\text{Found total amine value}) \times (\text{Found secondary} + \text{tertiary amine value})}{(\text{Found total amine value})} \times 100 \quad \text{formula (3)}$$

<Iodine Value Retention Rate>

For the unsaturated aliphatic primary amine and the nitrile of starting material, iodine value was measured by wijs-cyclohexane method. The value obtained was converted to molecular weight to determine iodine value retention rate according to the following formula (2).

$$\text{Iodine value retention rate}(\%) = \frac{\begin{pmatrix} \text{Iodine value} \\ \text{of} \\ \text{unsaturated} \\ \text{aliphatic} \\ \text{primary amine} \end{pmatrix} \times \begin{pmatrix} \text{Molecular} \\ \text{weight of} \\ \text{amine} \end{pmatrix}}{\begin{pmatrix} \text{Iodine value} \\ \text{of} \\ \text{unsaturated} \\ \text{aliphatic nitrile} \end{pmatrix} \times \begin{pmatrix} \text{Molecular} \\ \text{weight of} \\ \text{nitrile} \end{pmatrix}} \times 100 \quad \text{formula (2)}$$

-Solidification Point-

The solidification point of the unsaturated aliphatic primary amine was measured according to the standard method of analysis of oils and fats 2.2.5.2-1996 (Shukoff's method).

Comparative Example 1

The conversion reaction to amines was performed in the same way as in Example 1 except that para-toluamide was not added to obtain an unsaturated aliphatic primary amine. For the unsaturated aliphatic primary amine, the amine conversion rate, purity (selectivity to primary amine), iodine value retention rate, and solidification point were evaluated in the same way as in Example 1, and whether turbidity or scum was generated or not was observed visually. The results are shown in Table 3.

Comparative Examples 2 to 4 and 6 to 10

The conversion reactions to amines were performed in the same way as in Example 1 except that para-toluamide or benzamide was added in an amount shown in Tables 3 and 4 and ammonia and hydrogen were maintained to the pressure ratio shown in Tables 3 and 4 to obtain unsaturated aliphatic primary amines. For the unsaturated aliphatic primary amines, the amine conversion rate, purity (selectivity to primary amine), iodine value retention rate, and solidification point were evaluated in the same way as in Example 1, and whether turbidity or scum was generated or not was observed visually. The results are shown in Tables 3 and 4.

Comparative Example 5

The conversion reaction to amines was performed in the same way as in Example 1 except that para-toluamide was changed to oleylamide. The amine conversion rate, purity (selectivity to primary amine), iodine value retention rate, and solidification point were evaluated in the same way as in Example 1, and whether turbidity or scum was generated or not was observed visually. The results are shown in Table 3.

TABLE 1

|  | Example 1 | Example 2 | Example 3 | Example 4 | Example 5 | Example 6 |
|---|---|---|---|---|---|---|
| Aromatic carboxylic acid amide | para-toluamide | para-toluamide | para-toluamide | benzamide | benzamide | benzamide |
| Amount added (parts by weight) based on 100 parts by weight of the nitrile of starting material | 0.07 | 0.15 | 0.15 | 0.07 | 0.15 | 0.15 |

TABLE 1-continued

|  | Example 1 | Example 2 | Example 3 | Example 4 | Example 5 | Example 6 |
|---|---|---|---|---|---|---|
| Pressure ratio of ammonia to hydrogen | 6/4 | 6/4 | 8/2 | 6/4 | 6/4 | 8/2 |
| Amine conversion rate (%) | 99 | 97 | 97 | 98 | 97 | 97 |
| Primary amine purity (%) | 97 | 95 | 96 | 97 | 97 | 95 |
| Iodine value retention rate (%) | 98.9 | 99.3 | 97.7 | 97.1 | 98.6 | 98.2 |
| Solidification point (° C.) | 8 | 8 | 8 | 9 | 8 | 9 |
| Generation of turbidity or scum | None | None | None | None | None | None |

TABLE 2

|  | Example 7 | Example 8 | Example 9 | Example 10 | Example 11 | Example 12 |
|---|---|---|---|---|---|---|
| Aromatic carboxylic acid amide | para-toluamide | para-toluamide | para-toluamide | benzamide | benzamide | para-toluamide |
| Amount added (parts by weight) based on 100 parts by weight of the nitrile of starting material | 0.05 | 1.00 | 0.01 | 1.00 | 0.01 | 0.50 |
| Pressure ratio of ammonia to hydrogen | 6/4 | 6/4 | 6/4 | 6/4 | 6/4 | 7/3 |
| Amine conversion rate (%) | 99 | 95 | 99 | 95 | 98 | 96 |
| Primary amine purity (%) | 98 | 97 | 97 | 97 | 96 | 96 |
| Iodine value retention rate (%) | 97.1 | 99.5 | 95.1 | 99.3 | 95.0 | 98.9 |
| Solidification point (° C.) | 9 | 7 | 10 | 8 | 10 | 8 |
| Generation of turbidity or scum | None | None | None | None | None | None |

TABLE 3

|  | Comparative Example 1 | Comparative Example 2 | Comparative Example 3 | Comparative Example 4 | Comparative Example 5 |
|---|---|---|---|---|---|
| Aromatic carboxylic acid amide | — | para-toluamide | para-toluamide | para-toluamide | oleylamide |
| Amount added (parts by weight based on 100 parts by weight of the nitrile of starting material | 0 | 1.50 | 0.07 | 0.07 | 0.07 |
| Pressure ratio of ammonia to hydrogen | 6/4 | 6/4 | 5/5 | 9/1 | 6/4 |
| Amine conversion rate (%) | 98 | 68 | 97 | 81 | 98 |
| Primary amine purity (%) | 97 | 88 | 94 | 98 | 97 |
| Iodine value retention rate (%) | 89.4 | 98.5 | 88.9 | 94.1 | 98.0 |
| Solidification point (° C.) | 17 | 5 | 12 | 7 | 10 |
| Generation of turbidity or scum | None | None | None | None | observed |

TABLE 4

|  | Comparative Example 6 | Comparative Example 7 | Comparative Example 8 | Comparative Example 9 | Comparative Example 10 |
|---|---|---|---|---|---|
| Aromatic carboxylic acid amide | benzamide | benzamide | benzamide | para-toluamide | benzamide |
| Amount added (parts by weight) based on 100 parts by weight of the nitrile of starting material | 1.50 | 0.07 | 0.07 | 1.10 | 1.10 |
| Pressure ratio of ammonia to hydrogen | 6/4 | 5/5 | 9/1 | 6/4 | 6/4 |
| Amine conversion rate (%) | 65 | 98 | 79 | 86 | 87 |
| Primary amine purity (%) | 93 | 94 | 97 | 98 | 97 |
| Iodine value retention rate (%) | 99.0 | 89.2 | 94.5 | 97.7 | 97.1 |
| Solidification point (° C.) | 6 | 12 | 8 | 6 | 7 |
| Generation of turbidity or scum | None | None | None | None | None |

From the results of Tables 1 to 4, it was found that the unsaturated aliphatic primary amines, prepared by the production methods of Examples 1 to 12 in which 0.01 parts by weight to 1.0 part by weight of aromatic carboxylic acid amide was added based on 100 parts by weight of the nitrile of starting material and the pressure ratio of ammonia to hydrogen was adjusted to 8/2 to 6/4, are of high quality with a high amine conversion rate, purity, and iodine value retention rate, and excellent in handleability due to a low solidification point, and that the appearance is satisfactory since turbidity or scum was not generated.

INDUSTRIAL APPLICABILITY

Since the method for producing an unsaturated aliphatic primary amine of the present invention suppresses the generation of saturated aliphatic primary amine as a by-product, does not generate turbidity or scum, and can produce an unsaturated aliphatic primary amine with a low solidification point efficiently, it is suitable as a method for producing an unsaturated aliphatic primary amine in industrial scale.

In addition, the unsaturated aliphatic primary amine produced by the method for producing an unsaturated aliphatic primary amine of the present invention is of high quality and is excellent in handleability due to a low solidification point. Thus, the unsaturated aliphatic primary amine can suitably be used in a variety of applications as an intermediate of surfactant, dispersant, agricultural chemical, disinfectant, antistatic agent, textile treating agent, etc.

What is claimed is:

1. A method for producing an unsaturated aliphatic primary amine comprising
   subjecting an unsaturated aliphatic nitrile having 16 to 22 carbon atoms to hydrogen reduction in the presence of ammonia using a hydrogenation catalyst to produce an unsaturated aliphatic primary amine,
   wherein 0.01 parts by weight to 1.0 part by weight of aromatic carboxylic acid amide is added based on 100 parts by weight of the unsaturated aliphatic nitrile, and a partial pressure ratio of ammonia to hydrogen is adjusted to 8/2 to 6/4.

2. The method for producing an unsaturated aliphatic primary amine according to claim 1, wherein the aromatic carboxylic acid amide is one of para-toluamide and benzamide.

* * * * *